(12) United States Patent
Pavliak et al.

(10) Patent No.: US 6,355,625 B1
(45) Date of Patent: Mar. 12, 2002

(54) COMPOSITIONS OF β-GLUCANS AND SPECIFIC IGIV

(75) Inventors: Viliam Pavliak, Pittsford, NY (US); Ali Ibrahim Fattom, Rockville; Robert B. Naso, Gaithersburg, both of MD (US)

(73) Assignee: Nabi, Rockville, MD (US)

( * ) Notice: Subject to any disclaimer, the term of this patent is extended or adjusted under 35 U.S.C. 154(b) by 0 days.

(21) Appl. No.: 09/395,360

(22) Filed: Sep. 14, 1999

Related U.S. Application Data

(60) Provisional application No. 60/100,146, filed on Sep. 14, 1998.

(51) Int. Cl.⁷ .................. A61K 31/715; A61K 31/66; A61K 39/395
(52) U.S. Cl. .............. 514/54; 514/75; 424/130.1; 424/165.1; 424/169.1
(58) Field of Search ............ 514/54, 75; 424/130.1, 424/165.1, 169.1

(56) References Cited

U.S. PATENT DOCUMENTS

| | | | | |
|---|---|---|---|---|
| 4,739,046 A | * | 4/1988 | Di Luzio | 536/117 |
| 4,818,752 A | * | 4/1989 | Williams et al. | 514/54 |
| 4,833,131 A | * | 5/1989 | Williams et al. | 514/54 |
| 4,900,722 A | * | 2/1990 | Williams et al. | 514/54 |
| 5,032,401 A | * | 7/1991 | Jama et al. | 424/426 |
| 5,401,727 A | * | 3/1995 | Rorstad et al. | 514/54 |
| 5,607,677 A | * | 3/1997 | Jamas et al. | 424/278.1 |
| 5,741,495 A | * | 4/1998 | Jamas et al. | 424/278.1 |
| 5,770,208 A | * | 6/1998 | Fattom et al. | 424/197.11 |
| 5,785,975 A | * | 7/1998 | Parikh | 424/278.1 |
| 5,961,975 A | * | 10/1999 | Fattom et al. | 424/165.1 |
| 6,194,161 B1 | * | 2/2001 | Fattom et al. | 435/7.1 |

FOREIGN PATENT DOCUMENTS

WO 96/14873 5/1996

OTHER PUBLICATIONS

Kossaczka et al. "Synthesis and immunological properties of Vi and Di–O–acetyl pectin protein conjugates with adipic acid dihydrazide as the linker", Infect. Immun., 65(6): 2088–2093, 1997.*

Ostroff et al. "A new beta–glucan based macrophage–targeted adjuvant", ACS Symp. Ser., vol. 469: 52–59, 1991.*

Penna et al.; "Pulmonary Metastases Neutralization and Tumor Rejection by In Vivo Administration of β Glucan and Bispecific Antibody"; Int. Journal Cancer; vol. 65; 1996; pp. 377–382.

Thibault et al.; "Tumor–infiltrating Lymphocytes can be Activated In Situ By Using In Vivo Activants Plus F(ab')₂ Bispecific Antibodies"; Int. Journal Cancer; vol. 67; 1996; pp. 232–237.

Figueras; "Influence of the Sequence of Administration of β–Glucans and a *Vibrio damsela* Vaccine on the Immune Response of Turbot (*Scophthalmus Maximus* L.)"; Veterinary Immunology and Immunopathology; vol. 64; 1998; pp. 59–68.

Wakshull et al.; "PGG–Glucan, a Soluble β–(1,3)–glucan, Enhances the Oxidative Burst Response, Microbicidal Activity, and Activates an NF-$_k$B–like Factor in Human PMN: Evidence for a Glycosphingolipid β–(1,3)–glucan Receptor"; Immunopharmacology; vol. 41; 1999; pp. 89–107.

* cited by examiner

Primary Examiner—Gary Geist
Assistant Examiner—Devesh Khare
(74) Attorney, Agent, or Firm—Foley & Lardner

(57) ABSTRACT

Compositions and kits comprising combinations of β-glucans and specific immunoglobulins are disclosed. The compositions and kits are useful in methods of preventing or treating infection by a pathogenic microorganism, in which β-glucan is administered to a subject, and specific antibodies to a pathogenic microorganism are introduced into the subject.

24 Claims, 4 Drawing Sheets

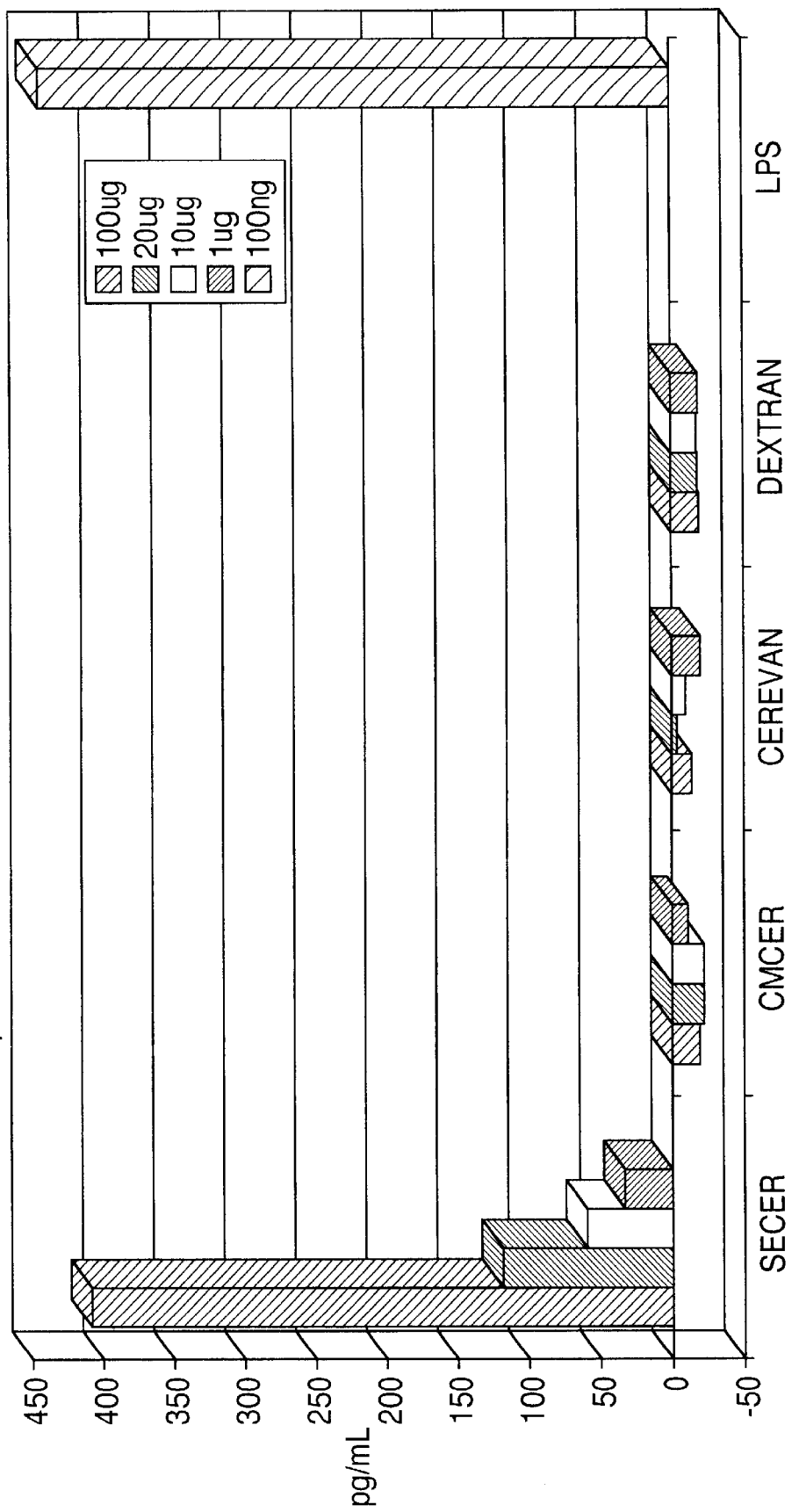

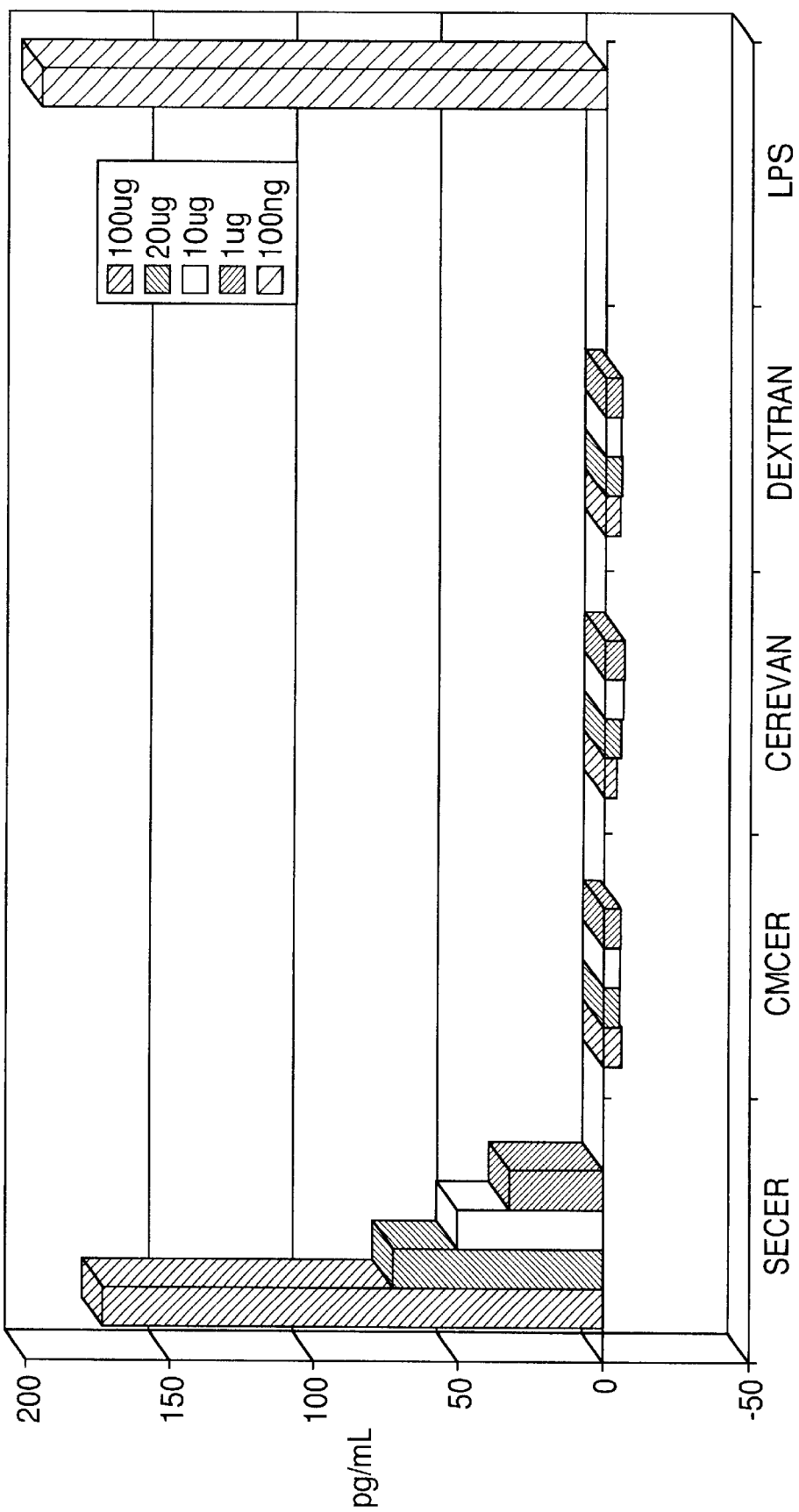
FIG. 1b EFFECT OF GLUCANS ON TNF-α RELEASE IN WHOLE HUMAN BLOOD.

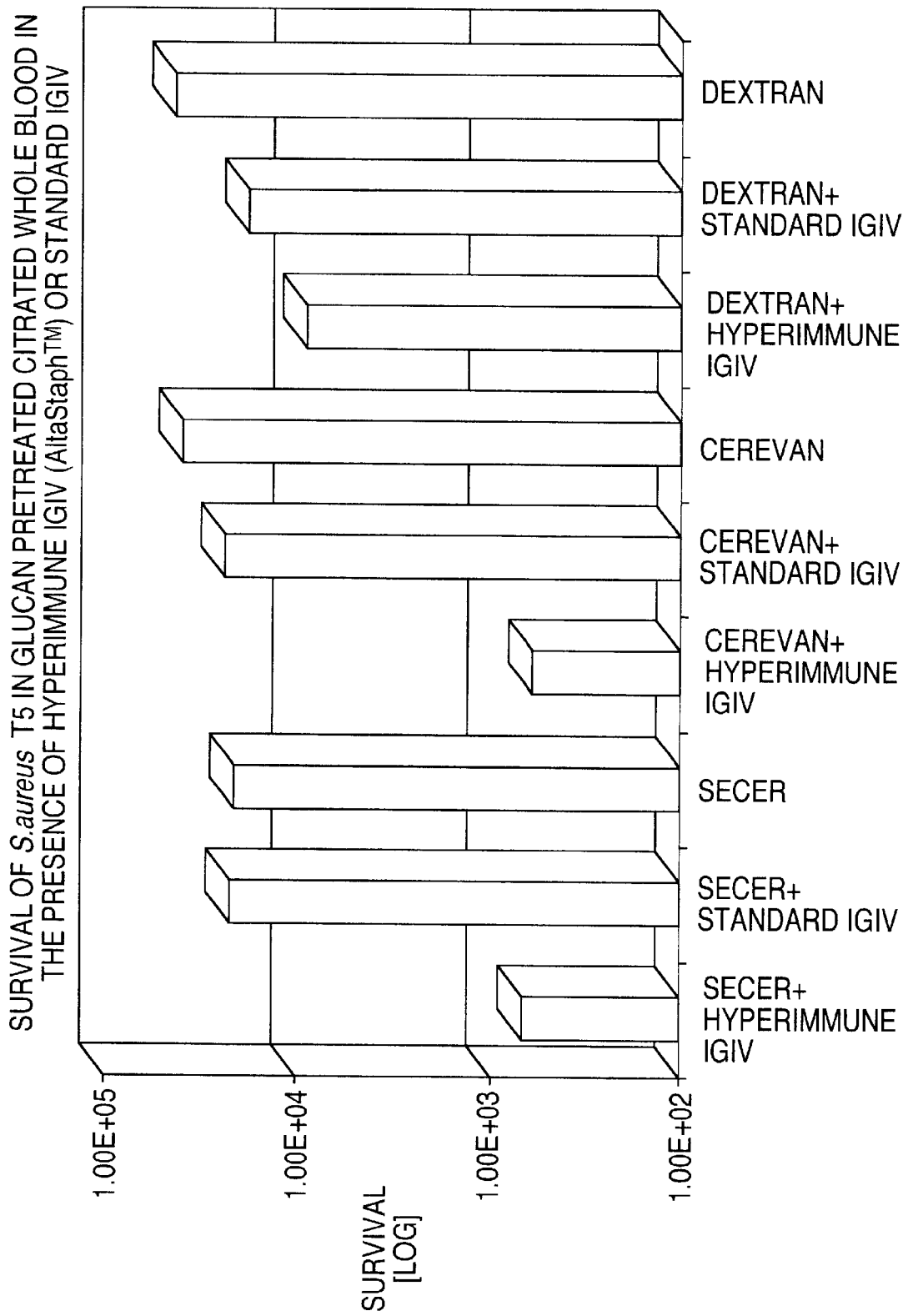

EFFECT OF AltaStaph™ TITRATION ON KILLING OF *S.aureus* REYNOLDS STRAIN IN β-GLUCAN PRETREATED WHOLE BLOOD.

COMPOSITIONS OF β-GLUCANS AND SPECIFIC IGIV

This appln claims benefit of Prov. No. 60/100,146 filed Sep. 14, 1998.

BACKGROUND OF THE INVENTION

The present invention relates to compositions comprising β-glucans and specific immunoglobulins, and to methods of therapy using the compositions.

β-glucans are major structural components of yeast, fungi, and algae. Glucans are polymers of glucose that exist in both branched and unbranched forms. The polymers can exist as single strands with helical conformation, or as a complex of multiple strands that form a multi-stranded helix stabilized by hydrogen bonding.

β-glucans have been shown to have an effect upon various aspects of the immune response, such as humoral and cell-mediated immunity. When β-glucans are administered to experimental animals, the animals exhibit a wide range of immunomodulating and immunostimulating biological activities. These include nonspecific resistance against a variety of pathogenic challenges, promotion of wound healing, adjuvant effects when coadministered with any of bacterial, fungal, protozoal, or viral antigens, prolonged survival time in tumor-bearing animals, enhancement of bone marrow recovery and survival of lethally-irradiated mice, and reduction of serum cholesterol levels.

Administration of β-glucans, particularly (1→3)β-D-glucans, enhances host resistance to a variety of experimentally-induced bacterial (*S. aureus, E. coli, K. pneunomiae, S. pyogenes, M. tuberculosis, M. pyogenes*), viral (Murin viral hepatitis, Venezuelan equine encephalomyelitis virus, HIV), fungal (*C. albicans, C. neoformans*) and parasitic infections. β-glucans exert a significant beneficial effect on infectious episodes in animals with chemotherapy-induced immunosuppression.

All glucans, especially the soluble (1→3)β-glucans, and more particularly the branched (1→3)β-glucans, appear to be capable of inducing activation of macrophages and neutrophils, and are used as biological response mediators. Recent evidence suggests that the anti-infective efficacy of (1→3)β-glucans is attributable, at least in part, to macrophage activation induced by binding of the glucan to two specific receptors.

Studies of soluble β-glucans in animals and humans have shown them to be non-antigenic and non-virulent. While β-glucans induce toxicity, within certain ranges they can retain their activity in vivo without an unacceptable toxicity profile. β-glucans which do not induce high levels of cytokines in vivo generally exhibit lower toxicity at higher amounts, but also generally exhibit lower potency. However, the potential for particulate glucans in immunotherapy is tempered by findings that their intravenous injection is associated with undesirable side effects, including hepatosplenomegaly, granuloma formation and microembolism.

Conventional treatment of bacterial infection entails the administration of antibiotics and/or standard IGIV. Standard IGIV is a composition comprising non-specific immunoglobulin. It contains antibodies typically found in a donor population which has not been stimulated by immunization with specific antigens. Combinations of β-glucans with both antibiotics and standard IGIV have been reported. Reports of combinations of β-glucans with standard IGIV and zinc describe improved response to β-glucans as a result of a poorly-defined nonspecific stimulation of immune mechanisms by the standard IGIV and zinc, and combinations of the β-1,3-linked triple-helical glucans extracted from *S. cerevisiae* with conventional antibiotic therapies have demonstrated increased efficacy as compared to the β-glucan alone. No combination of β-glucan with antibodies specific to a single species of pathogenic microorganisms has been described. Indeed, where standard immunoglobulins and glucans have been combined, non-specific stimulation of immune mechanisms by the standard immunoglobulin, rather than any specific effect, has been credited with any observed differences in overall effect vis-a-vis the use of glucan alone. Soltys et al., *Veterinary Immunology and Immunopathology* 42:379–388 (1994).

SUMMARY OF THE INVENTION

It is an object of the present invention to provide a composition, for use in a method of preventing or treating infection by a pathogenic microorganism, comprising a combination of β-glucans and antibodies specific to a single species of pathogenic microorganism.

It is a further object of the present invention to provide a composition, for use in a method of preventing or treating infection by a pathogenic microorganism, comprising a combination of β-glucans and antibodies specific to *S. aureus*.

It is a particular object of the present invention to provide a composition, for use in a method of preventing or treating infection by a pathogenic microorganism, comprising a combination of β-glucans and antibodies specific to *S. aureus* Type 5 and/or Type 8 antigens and/or antibodies specific to a *S. aureus* antigen that comprises β-linked hexosamine, that contains no O-acetyl groups detectable by nuclear magnetic resonance spectroscopy and that reacts with antibodies to ATCC 55804. This latter antigen is denoted the 336 antigen and is disclosed in U.S. Pat. No. 5,770,208 issued Jun. 23, 1998.

It is yet another object of the present invention to provide a composition, for use in a method of preventing or treating infection by a pathogenic microorganism, comprising a combination of β-glucans and antibodies specific to *E. faecalis* and/or *E. faecium* antigens, particularly those antigens disclosed in U.S. application Ser. No. 08/949,757 filed Oct. 14, 1997.

It is a further object of the present invention to provide a composition, for use in a method of preventing or treating infection by a pathogenic microorganism, comprising a combination of β-glucans and antibodies specific to *S. epidermidis* antigens, particularly *S. epidermidis* antigens as disclosed in U.S. application Ser. No. 08/361,821.

These and other objects according to the invention are provided by a composition comprising a β-glucan and specific antibodies. The specific antibodies preferably are specific to antigens from one or more of Staphylococcus and Enterococcus. When the specific antibodies are specific to Staphylococcus, they preferably are specific to one or more of Type 5 antigen or Type 8 antigen of *S. aureus*, a *S. aureus* antigen that comprises β-linked hexosamine, that contains no O-acetyl groups detectable by nuclear magnetic resonance spectroscopy and that reacts with antibodies to ATCC 55804, and an antigen from *S. epidermidis*. When the specific antibodies are specific to Enterococcus, they preferably are specific to *E. faecium* or *E. faecalis*. Preferably, the β-glucan is a soluble β-glucan, and more preferably a chemically-derivatized β-glucan, particularly one that is selected from the group consisting of carboxymethyl glucan, sulfoethyl glucan, glucuronoglucan, glucan sulfate, phosphorylated glucan, and glucan amine. Preferred β-glucans are (1→3)β-glucans, particularly those that are branched.

The present invention also provides a kit that comprises a soluble β-glucan, specific antibodies, and instructions for sequential administration of the β-glucan and specific antibodies. The composition and kit are useful in a method of preventing or treating infection by a pathogenic microorganism, which comprises administering a soluble β-glucan to a subject, and introducing specific antibodies to a pathogenic microorganism into said subject. The specific antibodies may be introduced in the subject by vaccinating the subject with a vaccine, or they may be introduced by administering specific antibodies to the subject. In the latter case, the specific antibodies preferably comprise hyperimmune immunoglobulin.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A and 1B are bar graphs showing cytokine induction by glucans.

FIG. 2 is a bar graph that shows survival of Type 5 *S. aureus* in glucan-pretreated whole blood in the presence of specific antibodies or standard IGIV.

DESCRIPTION OF PREFERRED EMBODIMENTS

Figure 3:
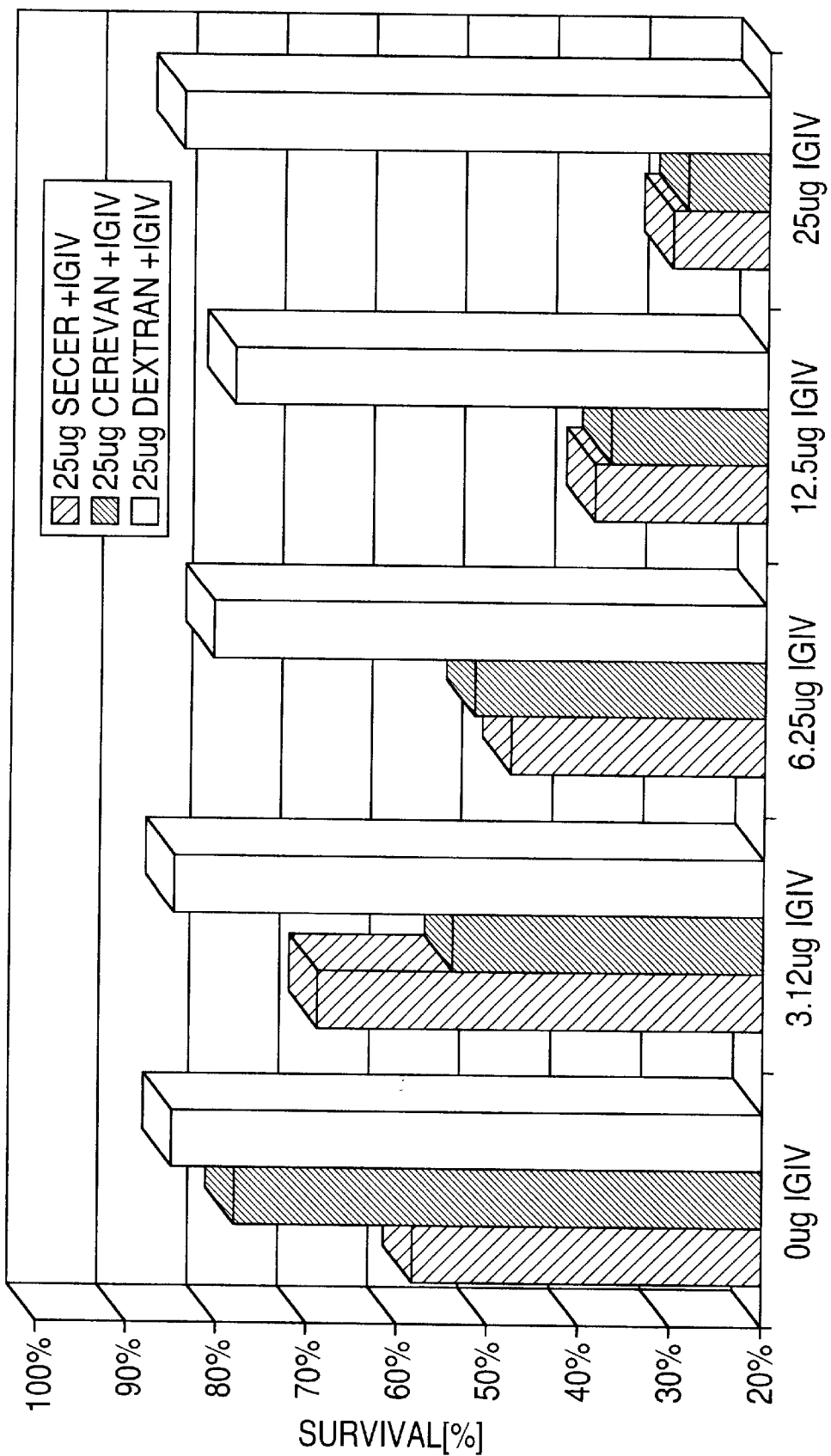
FIG. 3 is a bar graph that shows the effect of specific antibodies on killing of *S. aureus* (Reynolds strain) in β-glucan-pretreated whole blood.

It has been discovered, surprisingly, that a combination of β-glucans and specific antibodies produces an unexpected antimicrobial, more especially antibacterial, effect. In particular, the therapeutic effect of the combination was not known or predictable based on the separate actions of the β-glucans and the combined administration of β-glucans and standard IGIV, the administration of standard IGIV alone, or the administration of specific antibodies alone.

The term "specific antibodies" according to the invention comprises antibodies specific to a single species of bacteria, virus, fungi, protozoa, or cancer cells, and more preferably to one or more specific antigens expressed on the surface of that pathogen. Preferably the antibodies are opsonic antibodies, and the pathogen is capable of being opsonophagocytosed. In cases where a single species of pathogen is characterized by more than one clinically significant subtype, the specific antibodies may comprise antibodies against each of the clinically significant subtypes. Clinically significant subtypes may share a common antigen that elicits antibodies that are protective, in which case the shared antigen can be used to generate the specific antibodies according to the invention. Alternatively, the clinically significant subtypes may not share an antigen that elicits protective antibodies, in which case antigens specific to each subtype may be used to generate specific antibodies according to the invention.

In one preferred embodiment the specific antibodies are specific to one or more clinically significant strains and/or antigens of *S. aureus*. More particularly, these antibodies are specific to Type 5 and Type 8 antigens of *S. aureus*, as described in Fattom et al. *Inf. and Imm.* 58:2367–2374 (1990) and Fattom et al., *Inf. and Imm.* 64:1659–1665 (1996), or to a *S. aureus* antigen, denoted "336 antigen," that comprises β-linked hexosamine, that contains no O-acetyl groups detectable by nuclear magnetic resonance spectroscopy and that reacts with antibodies to ATCC 55804, which is described in Ser. No. 08/712,438, filed Sep. 11, 1996. (The contents of all documents cited herein are incorporated herein in their entirety by reference.) Specific antibodies to one, two or all three of these antigens may be combined in a single composition with β-glucans for administration.

In another preferred embodiment, antibodies specific to one or more clinically significant strains and/or antigens of *S. epidermidis* are combined with β-glucans for administration to a subject. A preferred *S. epidermidis* antigen is disclosed in application Ser. No. 08/361,821. In a further embodiment, specific antibodies to *S. aureus* Type 5, Type 8 and 336 antigens and specific antibodies to one or more clinically significant strains and/or antigens of *S. epidermidis* are combined with β-glucans in a composition.

In another embodiment, antibodies specific to one or more clinically significant strains and/or antigens of Enterococcus are combined with β-glucans. A preferred combination with Enterococcus employs *E. faecalis* and *E. faecium* antigens described in application Ser. No. (Attorney docket no. 018861/0155).

Specific antibodies can be induced in a subject prior to administration of P-glucan by vaccinating the subject with a composition comprising a specific antigen or antigens in a pharmaceutically acceptable carrier. Following vaccination it will take from 2–4 weeks for the subject to achieve an acceptable titer of specific antibodies to the injected antigen(s).

In a preferred embodiment, specific antibodies are administered to the subject in an immunoglobulin preparation obtained by administering a vaccine comprising the specific antigen or antigens to a subject who then acts as a source for Hiimmunoglobulin that contains antibodies directed against the specific antigen or antigens. A subject thus treated donates plasma from which immunoglobulin is obtained, via conventional plasma-fractionation methodology.

Alternatively, specific antibodies according to the invention are monoclonal or polyclonal antibodies, preferably monoclonal antibodies. Monoclonal antibody compositions contain, within detectable limits, only one species of antibody combining site capable of effectively binding to the specific antigen. Suitable antibodies in monoclonal form can be prepared using conventional hybridoma technology.

To form hybridomas from which a monoclonal antibody composition of the present invention is produced, a myeloma or other self-perpetuating cell line is fused with lymphocytes obtained from peripheral blood, lymph nodes or the spleen of a mammal hyperimmunized with the specific antigen of interest. It is preferred that the myeloma cell line be from the same species as the lymphocytes. Splenocytes are typically fused with myeloma cells using polyethylene glycol 1500. Fused hybrids are selected by their sensitivity to HAT. Hybridomas secreting the antibody molecules of this invention can be identified using an ELISA.

A Balb/C mouse spleen, human peripheral blood, lymph nodes or splenocytes are the preferred materials for use in preparing murine or human hybridomas. Suitable mouse myelomas for use in the present invention include the hypoxanthine-aminopterin-thymidine-sensitive (HAT) cell lines, a preferred myeloma being P3X63-Ag8.653. The preferred fusion partner for human monoclonal antibody production is SHM-D33, a heteromyeloma available from ATCC, Rockville, Md. under the designation CRL 1668.

A monoclonal antibody composition of the present invention can be produced by initiating a monoclonal hybridoma culture comprising a nutrient medium containing a hybridoma that secretes antibody molecules of the appropriate specificity. The culture is maintained under conditions and for a time period sufficient for the hybridoma to secrete the antibody molecules into the medium. The antibody-containing medium is then collected. The antibody molecules then can be isolated further by well known techniques.

Media useful for the preparation of these compositions are both well known in the art and commercially available, and include synthetic culture media, inbred mice and the like. An exemplary synthetic medium is Dulbecco's Minimal essential medium supplemented with 20% fetal calf serum. An exemplary inbred mouse strain is the Balb/c.

Other methods of preparing monoclonal antibody compositions are also contemplated, such as interspecies fusions, since it is primarily the antigen specificity of the antibodies that affects their utility in the present invention. Human lymphocytes obtained from infected individuals can be fused with a human myeloma cell line to produce hybridomas which can be screened for the production of antibodies that recognize the specific antigen. More preferable in this regard, however, is a process that does not entail the use of a biological sample from an infected human subject, for example, a process that uses a subject immunized with a vaccine as described above.

In a particularly preferred embodiment, monoclonal antibodies are produced to the specific antigen using methods similar to those described for type-specific antibodies to $S.$ $aureus$ Type 5 and Type 8. The purified monoclonal antibodies are characterized by bacterial agglutination assays using a collection of clinical isolates.

β-glucans can be divided into three groups: particulate glucans, gel-forming glucans, and soluble glucans. A major obstacle to the clinical utilization of particulate β-glucans is their relative lack of solubility in aqueous media. While topical or intralesional administration of insoluble particulate β-glucans induces no toxicity in mice, systemic or intravenous injection typically is associated with undesirable side effects such as hepatosplenomegaly, granuloma formation and microembolism.

These side effects are eliminated by solubilizing the β-glucan. Soluble derivatives are less toxic than other forms. Soluble derivatives can be prepared from insoluble glucan either by chemical or enzymatic hydrolysis or by chemical derivatization. Examples of chemically-derivatized, soluble β-glucans include carboxymethyl glucan, sulfoethyl glucan, glucuronoglucan, glucan sulfate, phosphorylated glucan, and glucan amine.

Some β-glucans induce significant levels of cytokines, while others either do not induce cytokines at all, or induce only minor levels of cytokines. In a preferred embodiment, the glucan is one that has been determined to activate macrophages or neutrophils, as determined by a simple in vitro assay. Combination of specific antibodies with both types of β-glucans results in an enhanced effect that is not predictable based on the separate actions of the β-glucans and the combined administration of 6-glucans and standard IGIV, the administration of standard IGIV alone, or the administration of specific antibodies alone.

The specific antibodies and β-glucans are the active ingredients in a composition(s), further comprising a pharmaceutically acceptable carrier for the active ingredients. In this regard, a pharmaceutically acceptable carrier is a material that can be used as a vehicle for administering a the active ingredients, because the material is inert or otherwise medically acceptable, as well as compatible with the active agents, in the context of parenteral administration, particularly intravenous administration. In addition to a suitable excipient, a pharmaceutically acceptable carrier can contain conventional additives like diluents, antioxidants, preservatives and solubilizing agents.

The β-glucans and specific antibodies can be administered separately or in a single composition. Preferably they are administered separately, with both the β-glucans and the specific antibodies being administered intravenously, subcutaneously, or intramuscularly. When administered separately, the β-glucans and the specific antibodies can be administered in any order, although it is preferred that the specific antibodies be administered first.

Pursuant to the present invention, such a composition can be administered to an at-risk, but otherwise healthy, subject thereby to provide protective immunity in that subject. Examples of at-risk subjects include patients requiring ongoing catheterization or patients undergoing joint replacement surgery. Alternatively, a composition within the present invention can be administered to a subject in which infection has already occurred in order to treat that infection in the subject.

The combination of β-glucans and specific antibodies produces a level of antibacterial effect that was not predictable based on the separate actions of the β-glucans and the specific antibodies. The effect has been demonstrated both in vitro and in vivo, and does not depend on any pyrogenic or inflammatory effects caused by the β-glucan. Combinations of specific antibodies with the same dose of dextran, an α-glucan, does not improve the antibacterial effect achieved with specific antibodies alone, nor does a combination of β-glucan with the same dose of standard IGIV improve the antibacterial effect seen with β-glucan alone.

It is particularly surprising that combinations of specific antibodies and β-glucans improve clearance from blood and protect against bacterial colonization of organs. The combination of hyperimmmune specific IgG with β-glucan at suboptimal doses significantly magnifies the clearance from blood and organs. On the other hand, neither β-glucan used separately, nor a combination of standard IGIV and β-glucans, protect against bacterial colonization of organs, and the protection against bacterial colonization of organs afforded by a combination of hyperimmune specific IgG and β-glucan significantly surpasses that achieved by the specific IgG alone. This is surprising given the lack of effect of β-glucans alone on colonization of organs and organ clearance. A combination of hyperimmune specific IgG and α-glucan does not result in an enhancement of organ clearance over that achieved by specific IgG alone.

The present invention is further described by reference to the following, illustrative examples.

EXAMPLE 1

Ability of β-glucans to Induce Cytokines

A variety of different β-glucans were tested, including a particulate glucan from $S.$ $cerevisiae$ (CEREVAN), a chemically-solubilized sulfoethyl-β-glucan (SECER), and a chemically-solubilized carboxymethyl-β-glucan (CMCER). The α-glucan dextran was used as a control.

The ability of each glucan to induce the cytokines TNFα and IL-1β was tested in vitro in human blood pretreated with the β-glucan and also in vivo in blood obtained from mice that had received intraperitoneal injections of 150 μg/day of the glucan on each of four days before testing. On the fifth day, blood was harvested and plasma prepared. Plasma samples were tested for the presence of the cytokines by ELISA. Of the three glucans tested, only SECER induced the two cytokines in the in vitro human blood experiment (FIGS. 1A and 1B) and none of the glucans induced the two cytokines in the in vivo mouse experiment.

EXAMPLE 2

In Vitro Effects of Combinations of β-glucans and S. aureus-specific IGIV

Combinations of the β-glucans of Example 1 with both nonspecific and S. aureus-specific IGIVs (IgGs) were tested in vitro. Nonspecific, or standard, IGIV containing low levels of S. aureus T5/T8 CP specific IgG and the hyperimmune S. aureus T5/T8 IGIV, AltaStaph™ (Nabi, Rockville, Md.), were used. Combinations with the α-glucan dextran were used as controls.

The combinations of glucan and the IGIVs were tested in a whole blood opsonopahagocytic assay. Citrated whole blood was incubated with the glucan preparation at 37° C. for 6 hours. The results showed more than a one log reduction of S. aureus bacterial counts in whole blood incubated with glucan supplemented with AltaStaph™, while samples supplemented with standard IGIV displayed the same level of activity obtained with β-glucan alone. The greater antibacterial effect achieved by the combination of glucan with specific IGIV was dependent on the concentration of specific IgG in the hyperimmune IGIV, and could be titrated out by reduction of S. aureus T5 CP specific IgG in the hyperimmune IGIV. The enhanced effect achieved with combinations was shared by both types of β-glucans evaluated (chemically-solubilized and particulate glucan). The results are shown in FIGS. 2 and 3.

EXAMPLE 3

In Vivo Effects of Combinations of β-glucans and S. aureus-specific IGIV on Survival in Mouse Lethality Model Combinations of β-glucan and hyperimmune IGIV were evaluated in vivo in a S. aureus T5 (strain ST021) mouse lethal challenge model using intraperitoneal injection of approximately 2×10^5 cfu/500 μl in 5% hog mucin/PBS. Optimal doses of both hyperimmune IGIV and β-glucan necessary to achieve approximately 50 and 100% protection against lethal challenge were determined. A dose of 150 μg and 50 μg of SECER were chosen to achieve 100% and 10–50% protection, respectively, in the S. aureus mouse lethal challenge model. For S. aureus T5 specific antibodies, a dose of 400 μg of S. aureus T5 specific antibodies administered subcutaneously 48 hours before lethal challenge was determined to be 100% protective, while a 200 μg dose gave 50% protection and a 100 μg dose, which was chosen as the suboptimal dose, was protective in the range 0–50% depending on variations in the bacterial challenge dose. Nonspecific hyperimmune IGIV, used as a control, was not protective.

Glucans were administered intramuscularly in a single injection, 24 hours before bacterial challenge. Hyperimmune IGIV was administered subcutaneously 48 hours before lethal challenge.

Combinations of β-glucan (SECER) and IGIV (standard or AltaStaph™), both at suboptimal protective dose, were evaluated. Results showed that the same dose of standard IGIV did not improve the protection level achieved by glucans alone. The combination of β-glucan with hyperimmune specific IGIV, however, induced a protective effect that was not predictable based on the separate activities of the β-glucan and specific antibodies. The results are shown in Table 1.

TABLE 1

Mortality of lethally challenged mice after treatment with combination of β-glucan and Hyperimmune IGIV (AltaStaph ™) or β-glucan and Standard IGIV.

| IGIV (Dose) (−48 hours from challenge) | Glucan (Dose) (−24 hours from challenge) | Accumulative Mortality (Hours Post-challenge) | | | | |
|---|---|---|---|---|---|---|
| | | 16 | 20 | 23 | 41 | 113 |
| AltaStaph ™ (200 μg T5 Ab 4.8 mg total IgG) | SECER 50 μg | 0/10 | 0/10 | 0/10 | 0/10 | 0/10 |
| AltaStaph ™ (200 μg T5 Ab 4.8 mg total IgG) | — | 5/10 | 5/10 | 5/10 | 5/10 | 5/10 |
| Standard IGIV (4.8 mg total IgG) | SECER 50 pg | 3/10 | 4/10 | 6/10 | 6/10 | 7/10 |
| Standard IGIV (4.8 mg total IgG) | — | 7/10 | 8/10 | 9/10 | 9/10 | 9/10 |
| — | SECER 50 μg | 4/10 | 5/10 | 9/10 | 9/10 | 9/10 |
| PBS | Dextran 150 μg/ | 6/10 | 6/10 | 7/10 | 8/10 | 8/10 |

EXAMPLE 4

In Vivo Effects of Combinations of β-glucans and S. aureus-specific IGIV on Bacterial Colonization of Organs The effect of combinations of β-glucan and hyperimmune IGIV (AltaStaph™) on colonization of organs was evaluated in mice challenged with sub-lethal doses (5×10^4 cfu/500 μl) of S. aureus T5 (strain ST021) administered intraperitoneally in 5% hog mucin. Antibodies were administered subcutaneously 48 hours before challenge. Glucans were administered intramuscularly 24 hours before bacterial challenge.

As shown in Table 2, AltaStaph™, alone or in combinations with β-glucan (SECER), prevented bacterial colonization of kidneys and livers (metastasis) in mice challenged with a sub-lethal dose of S. aureus T5 bacteria. Combination of AltaStaph™ with β-glucan was significantly more effective in preventing metastasis than AltaStaph™ alone, as shown by the geometric mean counts of positive samples (cfu/gm) and by the number of positive/total animals. This was quite surprising, since β-glucan alone does not protect against metastasis. Neither the 50% protective dose of β-glucan alone nor standard IGIV alone nor a combination of β-glucan and standard IGIV was able to protect survivors against metastasis.

TABLE 2

Effect of β-glucan plus hyperimmune IGIV combination on bacterial seeding in mice challenged wirth sub-lethal dose of *S. aureus* T5 bacteria, strain ST021.
Bacteria Organ Colonization Counts
(Geometric Mean of Positive Samples/Number of Positive Samples)

|  | Altastaph ™ + SECER | AltaStaph ™ + DEXTRAN | Stand. IGIV + SECER | Stand. IGIV DEXTRAN | SECER | DEXTRAN |
|---|---|---|---|---|---|---|
| Liver | 0.00E + 00<br>0/10 | 8.10E + 03<br>4/8[1] | 1.33E + 04<br>4/9[2] | 8.02E + 04<br>6/8[3] | 1.46E + 03<br>4/8[4] | 7.16E + 04<br>9/9[5] |
| Kidney | 0.00E + 00<br>0/10 | I.88E + 04<br>4/8 | 6.85E + 03<br>4/9 | 1.48E + 04<br>8/8 | 7.37E + 03<br>4/8 | 4.21E + 04<br>7/9 |

Altastaph ™ dose = 200 μg *S. aureus* T5 IgG (6.6 mg total IgG), Glucan dose = 50 μg, Standard IGIV dose 6.8 mg total IgG, Bacterial challenge dose = 5 × 10$^4$ cfu/0.5 mL.
[1]Two mice were found dead
[2]One mouse was found dead
[3]Two mice were found dead
[4]Two mice were found dead
[5]One mouse was found dead

EXAMPLE 5

In Vivo Effect of Combinations of *S. aureus* T5 Specific Antibodies with Suboptimal Doses of β-glucans on Survival in Mouse Lethality Model The effect of the administration of SECER and suboptimal concentrations of AltaStaph™ as a combination therapy was examined and results are shown in Table 3. The results of administration of hyperimmune IGIV at a suboptimal dose of 100 μg T5 IgG (0% protection) and glucan (60% protection) show a protective effect (90% protection) greater than expected based on the separate activities of the antibodies and the glucans.

TABLE 3

| *S. aureus* T5/T8 IgG dose | β-glucan | Accumulative Mortality Hours post-challenge | | | | |
|---|---|---|---|---|---|---|
| (AltaStaph ™) | (SECER) dose | 17 | 22 | 26 | 40 | 167 |
| 100 μg T5 IgG | 50 μg | 0/10 | 0/10 | 0/10 | 1/10 | 1/10 |
| 50 μg T5 IgG | 50 μg | 3/10 | 4/10 | 4/10 | 5/10 | 6/10 |
| 25 μg T5 IgG | 50 μg | 4/10 | 7/10 | 9/10 | 10/10 | 10/10 |
| 12.5 μg T5 IgG | 50 μg | 7/10 | 9/10 | 9/10 | 9/10 | 9/10 |
| 100 μg T5 IgG | — | 5/10 | 9/10 | 10/10 | 10/10 | 10/10 |
| 50 μg T5 IgG | — | 5/10 | 9/10 | 9/10 | 10/10 | 10/10 |
| 25 μg T5 IgG | — | 7/10 | 8/10 | 8/10 | 9/10 | 9/10 |
| 12.5 μg T5 IgG | — | 7/10 | 8/10 | 9/10 | 9/10 | 9/10 |
| — | 50 μg | 5/10 | 5/10 | 5/10 | 6/10 | 6/10 |
| 1X PBS | 1X PBS | 6/10 | 7/10 | 8/10 | 9/10 | 10/10 |

EXAMPLE 6

In Vivo Effect of Combinations of β-glucans and *Enterococcus faecalis*-specific IGIV in Mouse Bacteremia Model Combinations of β-glucans with hyperimmune IgGs purified from sera of rabbits immunized with *E. faecalis* polysaccharide conjugate vaccine, denoted E1 IgG, on bacteremia and colonization of organs was studied using the *E. faecalis* bacteremia mouse model. Hyperimmune E1 IgG reduces bacteremia in this model.

A suboptimal dose of E1 IgG containing 0.75 mg total IgG was combined with SECER. Control mice were treated with a combination of standard rabbit IgG (0.75 mg total IgG) with SECER, with E1 IgG combined with α-glucan or with SECER alone. Glucan doses of 150 μg were used for both α- and β-glucans.

Groups of ICR female mice were injected intraperitoneally on Day -1 with 0.75 mg IgG and intramuscularly with 150 μg glucan. On Day 0 the mice were challenged with 7.0×10$^7$ cfu/500 μl of *E. faecalis* strain 5–6 g.

The results are reported in Table 4, which reports the geometric mean of positive blood samples (cfu/ml), numbers of positive/total samples and % positive samples, respectively. A sample with counts of at least 10$^2$ cfu/ml was considered as positive.

TABLE 4

| | Treatment | | | |
|---|---|---|---|---|
| Time post challenge | E1 IgG + SECER | E1 IgG + Dextran | Standard IgG + SECER | SECER |
| 4 hours | 4.38E + 03<br>38/40<br>95% | 1.86E + 04<br>20/20<br>100% | 4.71E + 04<br>30/30<br>100% | 5.91E + 04<br>30/30<br>100% |
| 24 hours | 8.71E + 03<br>21/40<br>53% | 4.51E + 03<br>18/20<br>90% | 3.31E + 04<br>30/30<br>100% | 2.41E + 04<br>27/30<br>90% |
| 8 hours | 3.16E + 03<br>13/39<br>33% | 6.25E + 02<br>16/20<br>80% | 8.47E + 02<br>27/30<br>90% | 1.98E + 03<br>21/27<br>78% |
| 72 hours | 1.76E + 02<br>3/38<br>8% | 5.50E + 02<br>10/20<br>50% | 6.85E + 02<br>19/30<br>63% | 1.06E + 03<br>18/27<br>67% |
| 6 days | 5.39E + 02<br>5/38<br>13% | 2.86E + 02<br>8/20<br>40% | 7.44E + 02<br>18/30<br>60% | 1.36E + 03<br>22/27<br>82% |

The results showed that a combination of hyperimmune IgG and β-glucan (E1 IgG plus SECER) was far more effective than treatment with either standard IgG plus SECER or E1 IgG plus dextran. A significant difference was observed as early as 24 hours after treatment, as shown by the geometric mean of positive blood samples (cfu/ml), numbers of positive/total samples and % positive samples. The number of animals with positive blood samples in the E1 IgG plus SECER groups was reduced to 53% while the number of bacteremic animals in the control groups ranged from 90 to 100%.

Complimentary antibacterial effect of the combination on bacteremia was seen six days after treatment. At this point mice were sacrificed, and livers and kidneys were collected an evaluated for bacterial colonization. The results are reported in Table 5, which reports the geometric mean of positive blood samples (cfu/ml), numbers of positive/total samples and % positive samples, respectively. A sample with counts of at least $10^2$ was considered as positive.

TABLE 5

|  | E1 IgG + SECER | E1 IgG + Dextran | Standard IgG + SECER | |
|---|---|---|---|---|
| Kidney | 1.98E + 02 | 1.01E + 03 | 8.64E + 02 | 1.43E + 03 |
|  | 3/38 | 6/20 | 20/30 | 14/27 |
|  | 8% | 30% | 67% | 52% |
| Liver | 5.63E + 02 | 4.93E + 03 | 5.45E + 03 | 4.93E + 03 |
|  | 5/38 | 10/20 | 22/30 | 20/27 |
|  | 13% | 50% | 73% | 74% |

The results showed a positive effect of E1 IgG on clearance of kidney colonization with *E. faecalis*. The combination of E1 IgG with SECER significantly reduced colonization of the kidneys to 8% positive samples, compared to 30% positive sampled for E1 IgG plus dextran. Treatment of mice with SECER alone or in combination with standard IGIV reduced the number of positive kidney samples to 52% and 67%, respectively.

Similar results were found for liver. Only 13% of colonized livers were detected in the group of mice treated with E1 IgG plus SECER as compared to 50% positive samples in the group treated with E1 IgG plus dextran. Treatment with SECER alone, or in combination with standard IGIV did not clear colonization of livers (73 to 74% positive samples).

While the invention has been described in detail with respect to particular preferred embodiments, it should be understood that such description is presented by way of illustration and not limitation. Many changes and modifications within the scope of the present invention may be made without departing from the spirit thereof, and the invention includes all such modifications.

What is claimed is:

1. A composition comprising a β-glucan and hyperimmune specific IGIV.

2. A composition according to claim 1, wherein said β-glucan is a soluble β-glucan.

3. A composition according to claim 2, wherein said soluble β-glucan is a chemically-derivatized β-glucan.

4. A composition according to claim 3, wherein said chemically-derivatized β-glucan is selected from the group consisting of carboxymethyl glucan, sulfoethyl glucan, glucuronoglucan, glucan sulfate, phosphorylated glucan, and glucan amine.

5. A composition according to claim 1, wherein said β-glucan is a (1→3)β-glucan.

6. A composition according to claim 1, wherein said hyperimmune specific IGIV is specific to *S. aureus*.

7. A composition according to claim 6, comprising hyperimmune specific IGIV specific to a *S. aureus* antigen that comprises β-linked hexosamine, that contains no O-acetyl groups detectable by nuclear magnetic resonance spectroscopy and that reacts with antibodies to ATCC 55804.

8. A composition according to claim 6, comprising hyperimmune specific IGIV specific to a *S. epidermidis* antigen.

9. A method according to claim 6, comprising hyperimmune specific IGIV specific to a *S. aureus* antigen that comprises β-linked hexosamine, that contains no O-acetyl groups detectable by nuclear magnetic resonance spectroscopy and that reacts with antibodies to ATCC 55804.

10. A method according to claim 6, comprising hyperimmnune specific IGIV specific to a *S. epidermidis* antigen.

11. A composition according to claim 1, wherein said hyperimmune specific IGIV is specific to Type 5 antigen or Type 8 antigen.

12. A composition according to claim 1, wherein said hyperimmnune specific IGIV is specific to an Enterococcus antigen.

13. A composition according to claim 12, wherein said hyperimmune specific IGIV is specific to an *E. faecalis* or *E. faecium* antigen.

14. A method according to claim 12, wherein said hyperimmune specific IGIV is specific to an *E. faecalis* or *E. faecium* antigen.

15. A method according to claim 1, wherein said hyperimmune specific IGIV is specific to *S. aureus*.

16. A method according to claim 1, wherein said hyperimmune specific IGIV is specific to Type 5 antigen or Type 8 antigen.

17. A method according to claim 1, wherein said hyperimmune specific IGIV is specific to an Enterococcus antigen.

18. A composition according to claim 1, wherein said hyperimmune specific IGIV contains antibodies specific to a pathogenic microorganism.

19. A kit comprising:

a β-glucan;

hyperimmune specific IGIV; and instructions for sequential administration of said β-glucan and said hyperimmune specific IGIV.

20. A kit according to claim 19, wherein said hyperimmune specific IGIV contains antibodies specific to a pathogenic microorganism.

21. A method of preventing of treating infection by a pathogenic microorganism, comprising:

administering β-glucan to a subject; and introducing hyperimmnune specific IGIV into said subject.

22. A method according to claim 21, wherein said β-glucan is a soluble β-glucan.

23. A method according to claim 22, wherein said β-glucan is a chemically-derivatized β-glucan is selected from the group consisting of carboxymethyl glucan, sulfoethyl glucan, glucuronoglucan, glucan sulfate, phosphorylated glucan, and glucan amine.

24. A method according to claim 21, wherein said hyperimmune specific IGIV contains antibodies specific to a pathogenic microorganism.

* * * * *